United States Patent
Gasselin et al.

(10) Patent No.: US 11,147,754 B2
(45) Date of Patent: Oct. 19, 2021

(54) POWDER COMPOSITION COMPRISING HAIR DIRECT DYES

(71) Applicant: Kao Corporation, Tokyo (JP)

(72) Inventors: Celine Gasselin, Darmstadt (DE); Manuella Jourdain, Darmstadt (DE); Steven Breakspear, Darmstadt (DE); Bernd Noecker, Darmstadt (DE)

(73) Assignee: Kao Corporation, Tokyo (JP)

( * ) Notice: Subject to any disclaimer, the term of this patent is extended or adjusted under 35 U.S.C. 154(b) by 0 days.

(21) Appl. No.: 16/645,976

(22) PCT Filed: Sep. 20, 2018

(86) PCT No.: PCT/EP2018/075487
§ 371 (c)(1),
(2) Date: Mar. 10, 2020

(87) PCT Pub. No.: WO2019/057829
PCT Pub. Date: Mar. 28, 2019

(65) Prior Publication Data
US 2020/0197269 A1 Jun. 25, 2020

(30) Foreign Application Priority Data
Sep. 20, 2017 (EP) .................................. 17192079

(51) Int. Cl.
| | |
|---|---|
| *A61Q 5/10* | (2006.01) |
| *A61K 8/22* | (2006.01) |
| *A61K 8/35* | (2006.01) |
| *A61K 8/41* | (2006.01) |
| *A61K 8/49* | (2006.01) |
| *A61Q 5/08* | (2006.01) |

(52) U.S. Cl.
CPC ............... *A61K 8/22* (2013.01); *A61K 8/355* (2013.01); *A61K 8/41* (2013.01); *A61K 8/418* (2013.01); *A61K 8/4966* (2013.01); *A61Q 5/08* (2013.01); *A61Q 5/10* (2013.01)

(58) Field of Classification Search
CPC . A61Q 5/10; A61Q 5/065; A61Q 5/08; A61K 8/22; A61K 8/4946; A61K 8/347; A61K 2800/43; A61K 2800/31; A61K 8/355; A61K 8/732; A61K 8/4966; A61K 2800/432; A61K 8/418; A61K 8/41

USPC ............................................................. 8/405
See application file for complete search history.

(56) References Cited

U.S. PATENT DOCUMENTS

| | | | | |
|---|---|---|---|---|
| 6,054,591 A | * | 4/2000 | Aono ................... | A61K 31/415 548/319.1 |
| 6,190,421 B1 | * | 2/2001 | Rondeau ............... | A61K 8/415 8/407 |
| 2007/0000070 A1 | * | 1/2007 | Vena ................... | A45D 19/0066 8/405 |
| 2009/0217466 A1 | | 9/2009 | Barbieru et al. | |
| 2009/0249564 A1 | | 10/2009 | Barbieru et al. | |
| 2011/0277782 A1 | | 11/2011 | Iijima et al. | |
| 2012/0305021 A1 | | 12/2012 | Iijima et al. | |
| 2015/0007851 A1 | * | 1/2015 | Gebert ..................... | A61Q 5/10 132/208 |
| 2015/0045311 A1 | | 2/2015 | Antle | |
| 2015/0182441 A1 | * | 7/2015 | Goutsis ................. | A61K 8/362 132/208 |
| 2015/0250701 A1 | * | 9/2015 | Hamersky ................ | A61K 8/86 8/405 |
| 2017/0158781 A1 | | 6/2017 | Antle | |
| 2017/0196791 A1 | * | 7/2017 | Nojiri ..................... | A61Q 5/10 |

FOREIGN PATENT DOCUMENTS

| | | |
|---|---|---|
| DE | 42 33 874 A1 | 4/1994 |
| DE | 199 05 707 A1 | 8/2000 |
| EP | 2 883 531 A1 | 6/2015 |
| RU | 10-2008-0093115 A | 10/2008 |
| RU | 2 532 334 C2 | 3/2010 |
| RU | 2 615 385 C2 | 2/2013 |

OTHER PUBLICATIONS

International Search Report and Written Opinion dated Nov. 30, 2018 in PCT/EP2018/075487 filed on Sep. 20, 2018.

* cited by examiner

*Primary Examiner* — Eisa B Elhilo
(74) *Attorney, Agent, or Firm* — Oblon, McClelland, Maier & Neustadt, L.L.P.

(57) ABSTRACT

The present invention relates to a stable powder composition comprising hair direct dyes which is used for dyeing hair after mixing with one or more aqueous compositions. The composition comprises one or more direct dyes selected from HC Red 18, HC Blue 18, and HC Yellow 16, one or more alkanolamine as alkalizing agent, an organic and/or an inorganic pulverulent excipient.

19 Claims, No Drawings

POWDER COMPOSITION COMPRISING HAIR DIRECT DYES

FIELD OF THE INVENTION

The present invention relates to stable powder compositions comprising specific hair direct dyes which are used for dyeing hair after mixing with one or more aqueous compositions.

BACKGROUND OF THE INVENTION

Dyeing hair using direct dyes has been known for many years. Direct dyes are usually dissolved in an aqueous medium which is applied onto hair and after leaving it for a certain period of time, it is rinsed off from hair. There are also dyeing compositions available which may be left on the hair without rinsing them off. It has further been observed that some of the direct dyes may not be stably stored in such aqueous medium as they crystallize and precipitate during storage and, consequently, the dyeing performance of the composition is reduced and/or the shade intended to be achieved may not be the desired result of the dyeing process.

A known solution to the problem above is the addition of the direct dyes in pure powder form into aqueous compositions directly prior to use. This is not at all efficient as, at the time of use, the dissolving process may not be controlled and some of the dyes simply remain undissolved in the aqueous medium and, therefore, dyeing results are unsatisfactory. The reason for this may be that very small amount of dye powder is added so that it may not be observed if mixing and dissolution is complete. On the other hand, in order to dissolve solid dyes, large amount of aqueous medium may be required so that the target dye concentration may not be reached.

Another problem from the viewpoint of the hair dresser is that the HC dyes of the present invention exhibit a stark color difference when stored in powder and then later dissolved in aqueous medium. For example, HC Blue 18 appears in red color in powder form, but provides a blue color in dissolved form and also confers blue color to hair. This property is particularly confusing for the professional and amateur alike because it is impossible to predict the final color of the hair color composition and customer's hair prior to dissolving the dyes. Consequently, there may be several mixtures needed to meet the customers expectation before the coloring service may even begin. Thus, this results in higher cost of hair dresser service and often unsatisfied customers when the desired color effect is not achieved. Moreover, it is an environmental burden having to discard unnecessary hair color mixtures.

Examples of dye powders are disclosed in DE4233874 and DE19905707. However, the disclosures are silent on the dyes of the present invention. EP2883531 discloses HC dyes of the present invention, but is silent on the alkalizing agent of the present invention.

In order to solve the storage stability problem of the direct dyes in a powder medium which may as well be easily and effectively mixed into any aqueous and/or anhydrous compositions as well as to overcome the color change properties of the dyes, the inventors of the present invention have unexpectedly found out that when HC dyes are dispersed in an organic and/or an inorganic pulverulent excipient in the presence of alkanolamines as alkalizing agents both problems are overcome.

SUMMARY OF THE INVENTION

Thus, the first object of the present invention is a powder composition for treating keratin fibres, preferably human keratin fibres, especially human hair, characterized in that it comprises one or more direct dye(s) selected from HC Red 18, HC Blue 18 and HC Yellow 16, one or more alkanolamine(s) as alkalizing agent, an organic and/or inorganic pulverulent excipient.

In one embodiment, the composition comprises 10% or less, 7% or less, 5% or less, 3% or less and 2% or less, by weight, particularly 1% or less by weight water, calculated to the total composition.

The second object of the present invention is a method for coloring keratin fibers, preferably human keratin fibers, more preferably human hair, comprising the steps of:
a) mixing the powder composition as defined above into an aqueous composition comprising one or more conditioning ingredients immediately prior to application onto hair,
b) applying thus obtained composition onto hair and leaving it on the hair for a period from 1 to 45 min, and
c) rinsing-off the composition from hair,
d) optionally shampooing the hair,
e) optionally drying the hair.

The third object of the present invention is a method for bleaching and colouring keratin fibers, preferably human keratin fibers, more preferably human hair comprising the steps of
   a—mixing the powder composition as defined above with two other compositions wherein one of the compositions is an anhydrous powder composition comprising one or more persalts and the other composition is an aqueous composition comprising one or more oxidizing agent,
   b—applying thus obtained composition onto hair and leaving it on the hair for a period from 1 to 45 min, and
   c—rinsing-off the composition from hair,
   d—optionally shampooing the hair,
   e—optionally drying the hair.

A further object of the present invention is a kit for hair comprising a powder composition as defined above and an aqueous composition.

The kit as defined above advantageously comprises an aqueous composition selected from one or more of the following individually packed compositions:
   a—an aqueous composition comprising one or more conditioning ingredients
   b—an aqueous composition comprising one or more alkalizing agents
   c—an aqueous composition comprising one or more oxidative dye precursors,
   d—an aqueous composition comprising one or more oxidizing agents, and
   e—an anhydrous powder composition comprising one or more persalts.

DETAILED DESCRIPTION OF THE INVENTION

The composition of the present invention may comprise one or more solvent(s) for one or more direct dye(s) selected from water, ethanol, N-propanol, and isopropanol, and/or their mixtures, wherein preferably the total concentration of these solvent(s) and/or their mixtures is less than 10% by weight, more preferably less than 5% by weight, calculated to the total of the composition.

Under these conditions, the composition of the present invention still yields a freely flowing powder as illustrated in example 12.

From the viewpoint of enhancing stability of dye powders, it is more preferred that the composition is substantially anhydrous, as presented in examples 1 to 11, 13 to 24.

Substantially anhydrous within the meaning of the present invention denotes that the composition does not comprise added water, but water may be present because of bound water of the used raw materials and/or may exist because of hygroscopicity of the powder as a whole. Preferably, the composition of the has a water content of 10% or less, 7% or less, 5% or less, 3% or less and 2% or less, by weight, particularly 1% or less, calculated to the total composition.

The composition of the present invention may comprise one or more direct dyes other than HO Red 18, HO Blue 18 and HO Yellow 16 which may be selected from cationic, anionic and non-ionic dyes, in viewpoint of examples 14, and 16 to 21.

Suitable anionic direct dyes are Acid Black 1, Acid Blue 1, Acid Blue 3, Food Blue 5, Acid Blue 7, Acid Blue 9, Acid Blue 74, Acid Orange 3, Acid Orange 6, Acid Orange 7, Acid Orange 10, Acid Red 1, Acid Red 14, Acid Red 18, Acid Red 27, Acid Red 50, Acid Red 52, Acid Red 73, Acid Red 87, Acid Red 88, Acid Red 92, Acid Red 155, Acid Red 180, Acid Violet 9, Acid Violet 43, Acid Violet 49, Acid Yellow 1, Acid Yellow 23, Acid Yellow 3, Food Yellow No. 8, D&C Brown No. 1, D&C Green No. 5, D&C Green No. 8, D&C Orange No. 4, D&C Orange No. 10, D&C Orange No. 11, D&C Red No. 21, D&C Red No. 27, D&C Red No. 33, D&C Violet 2, D&C Yellow No. 7, D&C Yellow No. 8, D&C Yellow No. 10, FD&C Red 2, FD&C Red 40, FD&C Red No. 4, FD&C Yellow No. 6, FD&C Blue 1, Food Black 1, Food Black 2, Disperse Black 9 and Disperse Violet 1 and their alkali metal salts such as sodium, potassium. Among those, the most preferred anionic dyestuffs are Acid Red 52, DC Violet 2, DC Red 33, DC Orange 4, DC Red 27, DC Yellow 10, HC Blue 18, HC Red 18, and HC Yellow 16.

Suitable cationic dyes are in principle those available on the market for cosmetic hair colouring applications. For this purpose, special reference is made to the PCT application WO 95/15144 of Ciba-Geigy AG. Some examples to those are Basic Blue 6, Basic Blue 7, Basic Blue 9, Basic Blue 26, Basic Blue 41, Basic Blue 99, Basic Brown 4, Basic Brown 16, Basic Brown 17, Natural Brown 7, Basic Green 1, Basic Red 2, Basic Red 12 Basic Red 22, Basic Red 76, Basic Violet 1, Basic Violet 2, Basic Violet 3, Basic Violet 10, Basic Violet 14, Basic Yellow 57, Basic Red 51, Basic Yellow 87, HC Blue 17 and Basic Orange 31. The most preferred ones are Basic Red 51, Basic Yellow 87 Basic Orange 31, HC Blue 17 and Basic Blue 124.

Suitable neutral dyes including nitro dyes are HC Blue No. 2, HC Blue No. 4, HC Blue No. 5, HC Blue No. 6, HC Blue No. 7, HC Blue No. 8, HC Blue No. 9, HC Blue No. 10, HC Blue No. 11, HC Blue No. 12, HC Blue No. 13, HC Brown No. 1, HC Brown No. 2, HC Green No. 1, HC Orange No. 1, HC Orange No. 2, HC Orange No. 3, HC Orange No. 5, HC Red BN, HC Red No. 1, HC Red No. 3, HC Red No. 7, HC Red No. 8, HC Red No. 9, HC Red No. 10, HC Red No. 11, HC Red No. 13, HC Red No. 54, HC Red No. 14, HC Violet BS, HC Violet No. 1, HC Violet No. 2, HO Yellow No. 2, HO Yellow No. 4, HO Yellow No. 5, HO Yellow No. 6, HO Yellow No. 7, HO Yellow No. 8, HO Yellow No. 9, HO Yellow No. 10, HO Yellow No. 11, HO Yellow No. 12, HO Yellow No. 13, HO Yellow No. 14, HO Yellow No. 15, 2-Amino-6-chloro-4-nitrophenol, picramic acid, 1,2-Diamino-4-nitrobenzol, 1,4-Diamino-2-nitrobenzol, 3-Nitro-4-aminophenol, 1-Hydroxy-2-amino-3-nitrobenzol and 2-hydroxyethylpicramic acid.

The total concentration of one or more direct dyes (i.e., of HO Red 18, HO Blue 18, HO Yellow 16 and the above-described optional further dyes described) in the composition of the present invention preferably is 0.01% by weight or more, more preferably 0.05% by weight or more, further more preferably 0.1% by weight or more, calculated to the total of the composition, from the viewpoint of sufficiently dying the keratin fibers.

The total concentration of one or more direct dyes in the composition of the present invention preferably is 10% by weight or less, more preferably 9% by weight or less, further more preferably 7.5% by weight or less, further more preferably 6% by weight or less, even more preferably 4% by weight or less, calculated to the total of the composition, from the viewpoint of economic reasons and formulation freedom.

For attaining the above mentioned effects, the total concentration of one or more direct dyes in the composition of the present invention is preferably in the range of 0.01% to 10% by weight, preferably 0.05% to 9% by weight, more preferably 0.1% to 7.5% by weight, further more preferably 0.1% to 6% by weight, even more preferably 0.1% to 4% by weight, calculated to the total of the composition.

The composition of the present invention comprises one or more alkanolamine as an alkalizing agent from the viewpoint of alkalizing power, low hair damage, and color matching of powder and liquid hair dye composition. The suitable ones are alkanolamines according to the general structure

$R_4R_5R_6N$ wherein $R_4$, $R_5$ and $R_6$ are same or different H, $C_1$ to $C_4$ alkyl, $C_3$ to $C_4$ unsaturated alkyl, $C_3$ to $C_4$ branched alkyl, $C_1$ to $C_4$ hydroxy alkyl, $C_3$ to $C_4$ unsaturated hydroxy alkyl, $C_3$ to $C_4$ branched hydroxy alkyl, with the condition that at least one of $R_4$, $R_5$ or $R_6$ is different from H.

Suitable alkalizing agents are monoethanolamine, diethanolamine, triethanolamine, monoethanol methylamine, monoethanoldimethylamine, diethanolmethylamine, monoethanolethylamine, monoethanoldiethylamine, diethanolethylamine, monoethanolpropylamine, monoethanoldipropylamine, diethanolpropylamine, monoethanolbutylamine, 2-amino-2-methyl-1-propanol and diethanolbutylamine. Preferred alkalizing agents are monoethanolamine and/or 2-amino-2-methyl-1-propanol for cosmetic safety reasons. The most preferred is 2-amino-2-methyl-1-propanol abbreviated as AMP because it is solid at 25° C. and atmospheric pressure and may easily be mixed with other powder components, as presented in examples 1 to 6.

The total concentration of alkanolamines as alkalizing agent in the composition of the present invention preferably is 0.1% by weight or more, more preferably 0.2% by weight or more, further more preferably 0.25% by weight or more, still further more preferably 0.5% by weight or more, even more preferably 1% by weight or more, calculated to the total of the composition, from the viewpoint of color matching the powder dye composition to liquid dye composition.

The total concentration of alkanolamines as alkalizing agent in the composition of the present invention preferably is 25% by weight or less, more preferably 15% by weight or less, further more preferably 10% by weight or less, still further more preferably 9% by weight or less, calculated to the total of the composition, from the viewpoint of conferring low hair damage to keratin fibers, still maintaining a powder form for liquid alkanolamines at room temperature and atmospheric conditions, and cosmetic safety.

For attaining the above mentioned effect, the total concentration of alkanolamines as alkalizing agent in the composition of the present invention preferably is in the range of 0.1 to 25%, more preferably 0.2 to 15%, still more preferably 0.25 to 10%, further more preferably 0.5 to 9% by weight, even more preferably 1% to 9% by weight, calculated to the total of the composition, It is preferred from the viewpoint of color matching the powder dye compositions to liquid dye composition and keratin fiber color that the weight ratio of total concentration of HO Red 18, HO Blue 18 and HO Yellow 16 to total concentration of one or more alkanolamine(s) is in the range of 0.01 to 5, preferably 0.02 to 1.

The composition of the present invention comprises an organic and/or an inorganic pulverulent excipient in which the alkalizing agent and direct dyes are dispersed.

Suitable organic and/or an inorganic pulverulent excipients do not react with the dye and the alkalizing agent, and, thus, confer the powder a high degree of storage stability over an extended period of time. Suitable ones are, for example, diatomaceous earth, kaolin, bentonite, starch especially corn, tapioca, rice, wheat and potato, nylon powder, montmorillonit, gypsum, sawdust and perlite.

The total concentration of organic and/or an inorganic pulverulent excipient preferably is 50% by weight or more, more preferably 55% by weight or more, further more preferably 60% by weight or more, still further more preferably 65% by weight or more, even further more preferably 70% by weight or more, even more preferably 75% by weight or more, calculated to the total of the composition, from the viewpoint of achieving good dispersability of the direct dyes in the powder and quick dissolution of the powder.

The total concentration of organic and/or an inorganic pulverulent excipient preferably is 98% by weight or less, more preferably 95% by weight or less, further more preferably 90% by weight or less, calculated to the total of the composition, from the viewpoint of achieving good dispersability of the direct dyes in the powder and formulation freedom.

For attaining the above mentioned effects, the total concentration of organic and/or an inorganic pulverulent excipient preferably is in the range of 50% to 98% by weight, more preferably in the range of 55% to 95% by weight, further more preferably in the range of 60% to 90% by weight, still further more preferably 65% to 90% by weight, still further more preferably 70% to 90% by weight, even more preferably 75% to 90% by weight, calculated to the total of the composition.

The composition of the present invention is preferably free of persalts in viewpoint of undesired high lightening effect of the composition of the present invention.

The composition may comprise a second alkalizing agent other than one or more alkanolamine(s) selected from carbonate and/or bicarbonate salts with cations selected from sodium, potassium, ammonium and guanidine, from the viewpoint of achieving higher alkalinity, low hair damage, increased powder stability, and homogenous dispersibility of hair direct dyes.

Suitable ones are sodium carbonate, potassium carbonate, ammonium carbonate, guanidine carbonate, sodium bicarbonate, potassium bicarbonate, ammonium bicarbonate and guanidine bicarbonate.

The concentration of the second alkalizing agent is preferably in the range of 0.1% by weight or more, more preferably 0.25% by weight or more, still more preferably 0.5% by weight or more, most preferably 1% by weight or more, calculated to the total of the composition, from the viewpoint of low hair damage, increased powder stability, and homogeneous dispersibility of hair direct dyes.

The total concentration of the second alkalizing agent is preferably 10% by weight or less, more preferably 7.5% by weight or less, still more preferably 6% by weight or less, most preferably 5% by weight or less, calculated to the total of the composition, from the viewpoint of achieving higher alkalinity.

For attaining the above-mentioned effects, the concentration of the second alkalizing agent is preferably in the range of 0.1 to 10%, more preferably 0.25 to 7.5%, still more preferably 0.5 to 6% and most preferably 1 to 5% by weight calculated to the total composition, from the viewpoint of achieving higher alkalinity, low hair damage, increased powder stability, and homogenous dispersibility of hair direct dyes.

The composition may furthermore comprise sodium metasilicate as the third alakalizing agent from the viewpoint of from the viewpoint of achieving higher alkalinity, low hair damage, increased powder stability, and homogenous dispersibility of hair direct dyes, preferably at a concentration in the range of 0.1 to 5% by weight, calculated to the total of the composition.

The total alkalizing agent concentration in the composition, i.e. the sum of the alkanolamines, $2^{nd}$ and $3^{rd}$ alkalizing agent, preferably is 1% by weight or more, more preferably 2% by weight or more, calculated to the total of the composition, from the viewpoint of increased powder stability, homogenous dispersibility of hair direct dyes, and achieving a sufficient alkalinity for dyeing in combination with high alkaline concentration media.

The total alkalizing agent concentration in the composition, i.e. the sum of the alkanolamines, $2^{nd}$ and $3^{rd}$ alkalizing agent, preferably is 30% by weight or less, more preferably 25% by weight or less, calculated to the total of the composition, from the viewpoint of achieving a sufficient alkalinity for dyeing in combination with low alkaline concentration media.

For attaining the above-mentioned effects, the total alkalizing agent concentration in the composition, i.e. the sum of the alkanolamines, $2^{nd}$ and $3^{rd}$ alkalizing agent, preferably is in the range of 1% to 30% by weight, more preferably 2% to 25% by weight, calculated to the total of the composition.

The composition can additionally comprise polymers which may function as thickening and as well as conditioning agents. Suitable ones are non-ionic, anionic, amphoteric and cationic polymers. The cationic polymers are also especially suitable for conditioning agent.

Suitable non-limiting examples to non-ionic ones are cellulose and its derivatives such as methyl cellulose, hydroxyl ethyl cellulose, hydroxyl propyl cellulose, starch and its derivatives.

Suitable non-limiting examples to anionic ones are xanthan gum and its derivatives, acrylate polymers especially acrylates copolymer known with the trade name such as Balance, Luvimer, Rheocare and carbomer known with the trade names Carbopol, Suitable non-limiting examples to amphoteric polymers are Polyquaternium-22, Polyquaternium-37 and Polyquaternium-47.

Suitable non-limiting examples to cationic polymers are known with their CTFA adopted names Polyquaternium. Suitable and well known ones are Polyquaternium 1, Polyquaternium 2, Polyquaternium 4, Polyquaternium 5, Polyquaternium 6, Polyquaternium 7, Polyquaternium 8, Polyquaternium 9, Polyquaternium 10, Polyquaternium 11, Polyquaternium 12, Polyquaternium 13, Polyquaternium 14, Polyquaternium 15, Polyquaternium 16, Polyquaternium 17, Polyquaternium 18, Polyquaternium 19, Polyquaternium 20, Polyquaternium 24, Polyquaternium 27, Polyquaternium 28, Polyquaternium 29, Polyquaternium 30, Polyquaternium 31, Polyquaternium 32, Polyquaternium 33, Polyquaternium 34, Polyquaternium 35 and Polyquaternium 36, Polyquaternium 39, Polyquaternium 42, Polyquaternium 43, Polyquaternium 44, Polyquaternium 45, Polyquaternium 46, Polyquaternium 48, Polyquaternium-49, Polyquaternium 50, Polyquaternium 51, Polyquaternium 52, Polyquaternium 53, Polyquaternium 54, Polyquaternium 55, Polyquaternium 56, Polyquaternium 57, Polyquaternium 58, Polyquaternium 59, Polyquaternium 60, Polyquaternium 61, Polyquaternium 62, Polyquaternium 63, Polyquaternium 64, Polyquaternium 65, Polyquaternium 66, Polyquaternium 67, Polyquaternium 68, Polyquaternium 69, Polyquaternium-70, Polyquaternium 71, Polyquaternium 72, Polyquaternium 73, Polyquaternium 74, Polyquaternium 75, Polyquaternium 76, Polyquaternium 77, Polyquaternium 78, Polyquaternium-79, Polyquaternium 80, Polyquaternium 81, Polyquaternium 82, Polyquaternium 83, Polyquaternium 84, Polyquaternium 85, Polyquaternium 86 and Polyquaternium 87.

The presence of cationic polymer is exemplified in example 6.

Compositions according to the present invention can further comprise surfactants selected from anionic, non-ionic, amphoteric and/or cationic surfactants. The anionic, nonionic, amphoteric surfactants are used generally as emulsifier or solubilizer. The presence of surfactants may further contribute to miscibility of the compositions into another composition which may as well be anhydrous and/or aqueous. On the other hand, the cationic surfactants do provide the same benefits as the other surfactants but are at the same time particularly used as hair conditioners.

Anionic surfactants suitable are in principle known from the cleansing compositions. These are anionic surfactants of the sulfate, sulfonate, carboxylate and alkyl phosphate type, for example, the known $C_{10}$-$C_{18}$-alkyl sulfates, and in particular the respective ether sulfates, for example, $C_{12}$-$C_{14}$-alkyl ether sulfate, lauryl ether sulfate, especially with 1 to 4 ethylene oxide groups in the molecule, monoglyceride (ether) sulfates, fatty acid amide sulfates obtained by ethoxylation and subsequent sulfatation of fatty acid alkanolamides, and the alkali salts thereof, as well as the salts of long-chain mono- and dialkyl phosphates. Preferred anionic surfactants are alkyl sulphate surfactants especially lauryl sulphate and its salts.

Further suitable surfactants are nonionic surfactants. Non-limiting examples are long-chain fatty acid mono- and dialkanolamides, such as coco fatty acid mono- or diethanolamide and myristic fatty acid mono or diethanolamide, stearic acid mono or diethanolamide, alkyl polyglucosides with an alkyl group of 8 to 18 carbon atoms, and with 1 to 5 glucoside units, sorbitan esters, such as polyethylene glycol sorbitan stearic, palmitic, myristic and lauric acid esters, fatty acid polyglycol esters or poly-condensates of ethyleneoxide and propyleneoxide, as they are on the market, for example, under the trade name "Pluronics®", as well as fatty alcohol ethoxylates, $C_{10}$-$C_{22}$-fatty alcohol ethoxylates, known by the generic terms "Laureth", "Myristeth", "Oleth", "Ceteth", "Deceth", "Steareth" and "Ceteareth" according to the CTFA nomenclature, including addition of the number of ethylene oxide molecules, e.g., "Laureth-16": The average degree of ethoxylation thereby ranges between about 2.5 and about 100, preferably about 10 and about 30.

Suitable amphoteric surfactants are in particular the various known betaines such as alkyl betaines, fatty acid amidoalkyl betaines and sulfobetaines, for example, lauryl hydroxysulfobetaine; long-chain alkyl amino acids, such as cocoaminoacetate, cocoaminopropionate and sodium cocoamphopropionate and -acetate have also been proven suitable.

Suitable cationic surfactants are according to the general structure

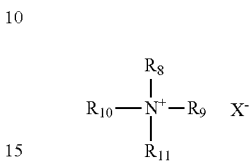

wherein $R_8$ is a saturated or unsaturated, branched or linear alkyl chain with 8-22 C atoms or

where $R_{12}$ is saturated or unsaturated, branched or linear alkyl chain with 7-21 C atoms and n has typical value of 1-4 or

where $R_{13}$ is saturated or unsaturated, branched or linear alkyl chain with 7-21 C atoms and n has typical value of 1-4, and $R_9$ is H or unsaturated or saturated, branched or linear alkyl chain with 1-22 C atoms or

or

where $R_{12}$, $R_{13}$ and n are same as above.

$R_{10}$ and $R_{11}$ are H or lower alkyl chain with 1 to 4 Carbon atoms, and X is typically chloride, bromide, methosulfate.

Typical examples of those ingredients are cetyl trimethyl ammonium chloride, stearyl trimonium chloride, dipalmitoyl dimonium chloride, distearyl dimethyl ammonium chloride, stearamidopropyl trimonuim chloride, dioleoylethyl dimethyl ammonium methosulfate, dioleoylethyl hydroxyethylmonium methosulfate.

The total concentration of one or more surfactants is in the range of 0.1 to 5%, preferably 0.2 to 4% and most preferably 0.2-2.5% by weight, calculated to the total composition.

Due to large particle size distribution and especially presence of very small particles, the composition may be dusty when dosing and/or mixing with other compositions. Therefore, in order to make the compositions dust free, a liquid dust binding and/or granulating agents may be added. These agents may be water immiscible oils such as natural oils, silicone oils and mineral oils. Total concentration of dust binding and/or granulating agents is in the range of 1% to 25% by weight, preferably 2% to 15% by weight, and more preferably 2.5% to 10% by weight, calculated to the total of the composition. All known natural oils are suitable as dust binding and/or granulating agents. Mineral oil (Liquid paraffin) is a preferred dust binding and/or granulating agent.

Silicone oils such as dimethicones and arylated silicones such as phenyl trmethicone may also suitably be used as dust binding and/or granulating agents.

The composition may comprise one or more aminosilicone as the conditioning agents, preferably selected from the following compounds
a. a compound according to the general structure

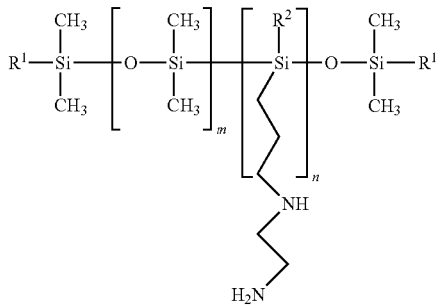

wherein R1 is selected from OH, OCH3, and/or O—Si—$(CH_3)_3$, R2 is selected from $CH_3$, $OCH_3$, O—(Si—$(CH_3)_2$) x-$R^1$, and/or O—Si—$(CH_3)_3$, with the provision that if $R^1$ or $R^2$ are selected from O—Si—$(CH_3)_3$, then all other $R^1$ or $R^2$ are selected from O—Si—$(CH_3)_3$ and/or $OCH_3$.
b. silicone graft copolymer comprising an organopolysiloxane segment as a main chain thereof and an unsaturated monomer-derived polymer segment as a side chain thereof, which is obtainable by firstly reacting an aminopropyl dimethicone with the thiolactone of acetyl homocysteine and then graft copolymerizing the thus obtained mercapto modified dimethicone with a mixture of N,Ndimethylacrylamide and N-t-butylacrylamide,
c. an organopolysiloxane, wherein at least two silicon atoms in an organopolysiloxane segments constituting a main chain of the organopolysiloxane are bound to poly(N-acylalkyleneimine) segments consisting of repeating units represented by the following general formula via alkylene group containing hetero atom:

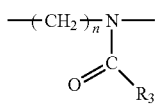

wherein $R_3$ is a hydrogen atom, an alkyl group having 1 to 22 carbon atoms, an aralkyl group, or an aryl group; and n is 2 or 3; wherein the number-average molecular weight of the poly-(N-acylalkyleneimine) segment is from 1,200 to 5,500, wherein the weight ratio of the organopolysiloxane segments (a) constituting the main chain to the poly-(N-acylalkyleneimine) segments (b) i.e., a/b is from 35/65 to 60/40, wherein the weight-average molecular weight of the adjacent poly-(N-acylalkyleneimine) segments is from 1,300 to 5,500, and wherein the weight-average molecular weight of the organopolysiloxane segment constituting the main chain is from 7,000 to 100,000.

Suitable examples are amodimethicone as known and delivered by various suppliers and polysilicone-9 supplied by Kao Corporation.

The total concentration of one or more amino silicones in the compositions is in the range of 0.01 to 2.5% by weight calculated to the total of the composition, in viewpoint of example 14 and 18.

The powder composition preferably comprises a flow enhancing agent in order to improve production and dosing. Suitable and well known one is colloidal silicium dioxide known with the trade name Aerosil which is available with various specific surface area. The preferred one in the present invention is Aerosil 280 which has a specific surface area of 280 m²/g. The flow enhancing agent is comprised at a concentration in the range of 0.1 to 3% by weight calculated to the total composition, as presented in examples 2 to 6.

The composition may further comprise chelating agents such as polyhydroxy acids preferably ethylenediamine tetra acetic acid and its salts especially sodium salt. The chelating agent is comprised at a concentration in the range of 0.1 to 5% by weight calculated to the total composition, as presented in examples 3, and 6.

Application of Powder Composition

The compositions of the present invention are mixed with another aqueous composition prior to application onto hair. The pH of the ready to use composition is in the range of 8 to 12, preferably 9 to 11 and more preferably 9.5 to 10.5.

The aspects below illustrate the application of the composition of the present invention in mixture. Thus, the composition of the present invention and this second composition form a kit in line with the further object of the present invention.

In one aspect of the present invention for the purpose of hair dyeing, the composition of the present invention is mixed into an aqueous composition. The aqueous composition may be a conventional hair conditioning and/or a cleansing composition. The hair conditioning compositions are known in general and widely being used. They are generally being a fatty alcohol and cationic surfactant based emulsion compositions which may comprise further known hair conditioners.

On the other hand, cleansing compositions are based on foaming cleansing surfactants such as anionic, non-ionic and amphoteric surfactants comprised generally at a concentration of approximately 20% by weight. Such compositions comprise furthermore hair conditioning compounds such as cationic polymers especially known with the CTFA adopted name as Polyquaternium.

The aspects above are illustrated in examples 1 to 3.

In another aspect of the present invention for hair dyeing the composition of the present invention is mixed into an aqueous composition comprising one or more alkalizing agent. The suitable alkalizing agents are alkyl or alkanol amines as disclosed above and aqueous ammonia.

The aspect is illustrated in example 2.

According to this aspect of the present invention the composition of the present invention is mixed into an aqueous composition comprising one or more oxidative dye precursors and/or one or more oxidizing agent.

Suitable oxidative dye precursors classes are p-phenylendiamines, p-aminophenols, and heterocyclic compounds such as diaminopyrazols and substituted pyrimidines, and suitable coupling substances are resorcinols, m-aminophenols, m-phenylendiamines, pyridines and substituted derivatives, and naphthols.

Non-limiting examples of the oxidative dye precursor compounds are p-phenylenediamine, p-aminophenol, 2,5-diamino-toluene, 2-n-propyl or 2-ethyl-p-phenylenediamine, 2,6-di-methyl-p-phenylene-diamine, 2-(2,5-diaminophenyl) ethanol, 1-amino-4-bis-(2'-hydroxy-ethyl)aminobenzene, 2-(2-hydroxyethyl amino)-5-aminotoluene, 4,4'-diaminodiphenylamine, 4-aminodiphenylamine, 2-amino-5-N,N-diethyl aminotoluene, 4-amino-N-ethyl-N-isopropyl aniline, 2-chloro-p-phenylenediamine, 1-β-hydroxyethyl-2,5-diamino-4-chlorobenzene, 1-β-hydroxyethyl-2,5-diamino-4-methyl benzene, 2-methoxy-p-phenylenediamine, N,N-diethyl-p-phenylenediamine, 1-amino-4-β-methoxyethyl aminobenzene, 1-dimethyl-amino-4-aminobenzene, 1-hydroxy-2,5-diamino-4-methyl benzene, 1-hydroxymethyl-2,5-diaminobenzene, 1,3-dimethyl-2,5-diaminobenzene, 1,4-diamino isopropyl benzene and/or 1-amino-4-β-hydroxypropyl aminobenzene, 1-hydroxyethyl-4,5-diaminopyrazole, 3,4-diamino-5-hydroxypyrazole, 3,5-diaminopyrazole, 3,5-diamino pyrazol-1-carboxamide, 3-amino-5-hydroxypyrazole, 1-phenyl-2-methyl pyrazole, 1-phenyl-3-methyl pyrazole-5-one, 3,5-dimethylpyrazole, 3,5-dimethyl pyrazole-1-methanol, 3,5-diamino-1,2,4-triazole, 4-aminophenol and the derivatives thereof such as 4-amino-3-methylphenol, 2-chloro-4-aminophenol, 2,6-dichloro-4-aminophenol, 2,4-diamino-phenol, 2,6-dibromo-4-aminophenol, tetraamino pyrimidines, triaminohydroxy pyrimidines, diaminomono- and -dihydroxy pyrimidines, aminotriazines, 5-amino salicylic acid and/or 1,2,4-triamino benzene, 2,5-diaminopyridine, 2,3-diaminopyridine, 2,6-diaminopyridine, 3-amino-2-methyl amino-6-methoxypyridine, 2-dimethyl-5-aminopyridine, 2-dimethyl aminoethyl-3-hydroxypyridine, 2-amino-4,6-dimethyl pyridine, 2-amino-3-hydroxypyridine, 3-amino-2(β-hydroxyethyl amino)-6-methoxy pyridine, 2,6-dimethyl amino-5-aminopyridine, 2-di(hydroxyethyl) amino-5-aminopyridine, 2-hydroxyethyl amino-5-aminopyridine, 4-hydroxy-2,5,6-triaminopyrimidine and/or the water-soluble salts thereof, and mixture thereof.

The total concentration of the dye precursors (developing substances) customarily ranges between 0.001 to 5%, preferably 0.01 to 4% and more preferably 0.05 to 3%, and most preferably 0.1 to 2% by weight, calculated to the total composition.

The aqueous composition comprising the oxidative dye precursor may further comprise coupling substances. The suitable non-limiting examples of the coupling substance if present in the composition A are 5-amino-2-methyl phenol, 2-methyl-5-hydroxyethylaminophenol, 2,4,-diaminophenoxyethanol, 2-amino-4-hydroxyethylaminoanisol, 2-methyl-5-amino-6-chlorphenol, 1,3-bis(2,4-diaminophenoxy)propane, 2-bis(2-hydroxyethyl)aminotoluene, 2-amino-5-methylphenol, resorcinol, 2-methyl-resorcinol, 4-chlororesorcinol, 2-amino-4-chlorophenol, 5-amino-4-methoxy-2-methyl phenol, 2-aminophenol, 3-amino-phenol, 1-methyl-2-hydroxy-4-aminobenzene, 3-N,N-dimethyl aminophenol, 2,6-dihydroxy-3,5-dimethoxypyridine, 5-amino-3-methylphenol, 6-amino-3-methylphenol, 1,3-diamino-benzene, 1-amino-3-(2'-hy-droxyethylamino)benzene, 1-amino-3-[bis(2'-hy-droxy-ethyl) amino]benzene, α-naphthol, 4,6-dichlororesorcinol, 1,3-diamino-toluene, 4-hydroxy-1,2-methylenedioxy benzene, 1,5-dihydroxy naphthalene, 1,6-dihydroxy naphthalene, 1,7-dihydroxy naphthalene, 2,7-dihydroxy naphthalene, 1-hydroxy-2-methyl naphthalene, 4-hydroxy-1,2-methyldioxy benzene, 2,4-diamino-3-chlorophenol, 5-amino-2-methoxyphenol and/or 1-methoxy-2-amino-4-(2'-hydroxyethyl amino)benzene or the water-soluble salts thereof and mixture thereof.

The coupling substance are present in approximately the same molecular proportions as the developing substances, i.e. at a total concentration in the range of 0.001 to 5%, preferably 0.01 to 4% and more preferably 0.05 to 3%, and most preferably 0.1 to 2% by weight, calculated to the total composition.

In one aspect of the present invention, the composition of the present invention is mixed into an aqueous composition comprising one or more oxidizing agents. The oxidizing agents suitable are hydrogen peroxide, urea peroxide, melamin peroxide or perborate salts. The most preferred is hydrogen peroxide. The aqueous composition comprises one or more oxidizing agents at a total concentration of 1 to 20% by weight, preferably 2 to 15%, more preferably 2 to 12% and most preferably 3 to 12% by weight, calculated to total of the aqueous composition. The aqueous composition may be in the form of a solution, thickened gel or an emulsion. Emulsion form is particularly preferred. The aqueous composition comprising one or more oxidizing agents has a pH in the range of 2 to 5.

This aspect is illustrated in example 4.

In one aspect of the present invention, the composition of the present invention comprises one or more persalts. Useful are sodium persulfate and potassium persulfate and ammonium persulfate, earth alkali peroxides such as magnesium peroxide, melamine peroxide or urea peroxide or phtolimidoperoxy hexanoic acid. The preferred persalts are sodium persulfate and potassium persulfate. The persalt is comprised in the anhydrous composition at a total concentration in the range of 10 to 80%, preferably 15 to 70%, more preferably 20 to 60% and most preferably 25 to 60% by weight, calculated to total of composition A.

The above composition is then mixed with an aqueous composition comprising one or more oxidizing agent as described above. This aspect is illustrated in example 4.

The following examples are to illustrate the invention but not to limit.

Example 1

| Ingredient | % by weight |
| --- | --- |
| Aminomethyl propanol | 8.4 |
| HC Red 18 | 2.0 |
| HC Blue 18 | 0.1 |
| HC Yellow 16 | 0.1 |
| Diatomaceous earth | to 100 |

The above composition was prepared by mixing all the ingredients in Diatomaceous earth.

Stability tests of the above composition at 5° C., 20° C., 40° C. and 50° C. did not show any instability during the test period of 6 months. Macroscopic evaluation showed no change in appearance of the powder composition.

The above composition was mixed with the following cleansing composition at a weight ratio of the Example 1 to cleansing composition 2:10.

| Ingredient | % by weight |
| --- | --- |
| Sodium Laureth Sulphate | 12.0 |
| Sodium lauroyl sarcosinate | 3.0 |
| Lauryl hydroxyl sultaine | 1.5 |
| Ethyl hexyl glycerine | 0.9 |
| Amodimethicone | 0.3 |
| Lactic acid | q.s. to pH 5.5 |
| Water | to 100 |

The resulting composition had a pH of 9.5.

The bleached human hair streak was washed with the obtained composition. The hair streak was colored red.

In the same way, the Example 1 was mixed into a hair conditioning composition having the following composition at a weight ratio of the Example 1 to conditioning composition 2:10.

| Ingredient | % by weight |
| --- | --- |
| Cetearyl alcohol | 10 |
| Cetrimonium chloride | 1 |
| Ceteareth-20 | 2 |
| Amodimethicone | 0.3 |
| Lactic acid | q.s. to pH 4.0 |
| Water | to 100 |

The resulting composition had a pH of 9.5.

The bleached human hair streak was treated with the obtained composition. The hair streak was colored red.

Example 2

| Ingredient | % by weight |
| --- | --- |
| Aminomethyl propanol | 8.4 |
| HC Red 18 | 1.5 |
| HC Blue 18 | 1.5 |
| HC Yellow 16 | 0.5 |
| Paraffin oil | 5.0 |
| Hydroxyethyl cellulose | 1.0 |
| Aerosil 280 | 1.5 |
| Diatomaceous earth | to 100 |

The above composition was prepared by mixing all the ingredients in Diatomaceous earth.

The above composition was mixed with the following oxidizing composition at a weight ratio of Example 2 to oxidizing composition 1 to 1.

| Ingredient | % by weight |
| --- | --- |
| Cetearyl Alcohol | 1.7 |
| Mineral Oil | 2 |
| Glycerin | 0.5 |
| Etidronic Acid | 0.2 |
| Salicylic Acid | 0.02 |
| Phosphoric acid | 0.3 |
| Sodium Lauryl Sulfate | 0.2 |
| Hydrogen Peroxide | 6.0 |
| Water | Ad 100 |

The above composition has a pH 3.5.

The resulting composition had a pH 9.8.

The human hair streak having a natural colour at level 6 was colored with the composition thus obtained with a processing time of 30 min. The hair was colored red-brown.

Additionally the Example 2 was mixed with the above oxidizing composition and the following oxidative dyeing composition at a weight ratio of 1:3:2 (Example 2: Oxidizing composition: oxidative dyeing composition).

| Ingredient | % by weight |
| --- | --- |
| Cetearyl alcohol | 12 |
| Sodium Cetearyl Sulfate | 1.5 |
| Cocamide MEA | 5 |
| Propylene Glycol Stearate SE | 0.6 |
| Oleth-5 | 5.0 |
| Oleic Acid | 2.5 |
| Propylene Glycol | 1.0 |
| Tetrasodium EDTA | 0.2 |
| Ammonium Chloride | 0.5 |
| Sodium Sulfite | 0.8 |
| Ammonium Hydroxide | 5.0 |
| Toluene-2,5-Diamine sulfate | 0.74 |
| Resorcinol | 0.1 |
| 4-Chlororesorcinol | 0.24 |
| m-Aminophenol | 0.0 |
| 4-Amino-2-Hydroxytoluene | 0.02 |
| Perfume | q.s. |
| Water | Ad 100 |

The resulting composition had a pH 9.9.

The human hair streak having a natural colour at level 6 was colored with the composition thus obtained with a processing time of 30 min. The hair was colored red-brown.

Furthermore, the Example 2 was mixed with the above oxidizing composition and the following oxidative dyeing composition at a weight ratio of 1:3:2 (Example 2: Oxidizing composition: oxidative dyeing composition).

| Ingredient | Active matter % |
| --- | --- |
| Cetearyl Alcohol | 9.0 |
| Oleyl Alcohol | 4.0 |
| Octyldodecanol | 2.0 |
| Ceteareth-20 | 4.0 |
| Argania Spinosa Kernel Oil | 0.1 |
| Tetrasodium Glutamate Diaceate | 0.1 |
| Ethanolamine | 5.0 |
| Ascorbic Acid | 1.0 |
| Disodium Phosphate | 0.5 |
| Allantoin | 0.5 |
| Toluene-2,5-Diamine Sulfate | 1.0 |
| Resorcinol | 0.4 |
| m-Aminophenol | 0.08 |
| 2-Amino-3-Hydroxypyridine | 0.02 |
| Perfume | q.s. |
| Water | Ad 100 |

The resulting composition had a pH 9.7.

The human hair streak having a natural colour at level 6 was colored with the composition thus obtained with a processing time of 30 min. The hair was colored red-brown.

In a further test, the Example 2 was mixed with the above oxidizing composition and the following oxidative dyeing composition at a weight ratio of 1:3:2 (Example 2: Oxidizing composition: oxidative dyeing composition).

| Ingredient | % by weight |
| --- | --- |
| Cetearyl alcohol | 9.0 |
| Sodium Cetearyl Sulfate | 1.5 |
| Cocamide MEA | 3.0 |
| Oleic Acid | 1.00 |
| Tetrasodium EDTA | 0.2 |
| Sodium Sulfite | 0.5 |
| Potassium Iodide | 5.0 |
| Toluene-2,5-Diamine Sulfate | 1.0 |
| Resorcinol | 0.3 |
| m-Aminophenol | 0.1 |
| 4-Amino-m-cresol | 0.1 |
| 2-Amino-4-Hydroxyethylaminoanisole Sulfate | 0.1 |
| 2-Amino-3-Hydoxypyridine | 0.1 |
| HC Yellow 2 | 0.1 |
| Perfume | q.s. |
| Water | Ad 100 |

The resulting composition had a pH 8.5.

The human hair streak having a natural colour at level 6 was colored with the composition thus obtained with a processing time of 30 min. The hair was colored reddish-brown.

Example 3

| Ingredient | % by weight |
| --- | --- |
| Aminomethyl propanol | 8.4 |
| HC Red 18 | 1.5 |
| HC Blue 18 | 1.5 |
| HC Yellow 16 | 0.5 |
| Aerosil 280 | 2.0 |
| Paraffin oil | 7.2 |
| Xantan gum | 0.2 |
| Carboxymethyl cellulose | 2.1 |
| Disodium EDTA | 2.0 |
| Sodium bicarbonate | 2.0 |
| Dimethicone 200 cSt | 2.0 |
| Sodium lauryl sulphate | 1.0 |
| Diatomaceous earth | to 100 |

The above composition was prepared by mixing all powder components first and afterwards the liquid components were added portion-wise and a dust free fine granular looking powder was obtained.

The composition was used to carry out all the dyeing examples disclosed under Example 2. The hair dyeing results were confirmed in the very similar way.

Example 4

| Ingredient | % by weight |
| --- | --- |
| Aminomethyl propanol | 5.0 |
| HC Red 18 | 0.4 |
| HC Yellow 16 | 0.1 |
| HC Blue 18 | 1.0 |
| Fragrance | q.s. |
| Diatomaceous Earth | to 100 |

The above composition was prepared by mixing all ingredients in Diatomaceous Earth. The above composition comprises less than 1% by weight water.

The above composition was mixed with an anhydrous bleaching composition of the following composition and the above under Example 2 presented oxidizing composition at a weight ratio of 1:2:3.

| Ingredient | % by weight |
| --- | --- |
| Ammonium persulfate | 21.00 |
| Potassium persulfate | 36.00 |
| Sodium metasilicate | 11.00 |
| Diatomaceous Earth | 21.00 |
| Aerosil 380 | 1.00 |
| Liquid paraffin | 10.00 |

The resulting composition had a pH of 9.8. Hair was bleached and coloured brownish.

Examples 5-12

A powder hair dye composition was prepared in the same manner as in previous examples. Color evaluation of the powders was done as follows: In a cylindrical container sufficient powder hair dye composition was put to uniformly cover the bottom, the surface was uniformly leveled with a spatula. A glass slide with a thickness of about 1 mm was then put thereon, and measurement was carried out from above the glass slide using a color-difference meter (Datacolor 45G) using the CIE colorimetric system (L*,a*,b*,h).

To 1 g of powder hair dye composition shown in Tables 1 to 2, 2 g of 6% by weight aqueous solution of ammonia was added, and the obtained mixture was stirred until being uniform for about a minute with a spatula to prepare a hair dye mixture. To about 1 g of untreated hair bundle purchased from Fischbach+Miller Haar, Laupheim, Germany, 2.5 g of hair dye mixed liquid was applied and spread by rubbing with hands over a minute. The hair was allowed to stand at 30° C. for 20 minutes at 40° C., washed with a commercially available shampoo available under the brand name Goldwell Dualsenses Color Shampoo for 30 seconds, wiped with a towel, and dried with cold air using a blow-drier. The hue of a hair bundle immediately after being treated with the hair dye mixture, washed and dried was measured using a color-difference meter by the CIE colorimetric system (L*, a*,b*,h), and the color difference (ΔE*) and hue difference (Δh) from the above powder hair dye composition were calculated by the following formula.

$$\Delta E^* = \sqrt{(L_1^* - L_0^*)^2 + (a_1^* - a_0^*)^2 + (b_1^* - b_0^*)^2}$$

[where $h_0$ represent a h value of a powder hair dye composition, and $h_1$ represents a h value of hair immediately after hair dyeing. The h value is a hue angle and 0°=360°. Because of this, when Δh is above 180°, a value of 360°-Δh is taken.]

TABLE 1

| | | Example 5 | Comparative Example 5 | Example 6 | Comparative Example 6 | Example 7 | Comparative Example 7 |
| --- | --- | --- | --- | --- | --- | --- | --- |
| Composition (% by weight) | HC Blue 18 | 2.0 | 2.0 | — | — | — | — |
| | HC Red 18 | — | — | 2.0 | 2.0 | — | — |
| | HC Yellow 16 | — | — | — | — | 2.0 | 2.0 |
| | 2-amino methyl propanol | 8.4 | — | 8.4 | — | 8.4 | — |
| | Sodium carbonate | — | 8.4 | — | 8.4 | — | 8.4 |
| | Diatomaceous earth | Ad 100.0 | Ad 100.0 | Ad 100.0 | Ad 100.0 | Ad 100.0 | Ad 100.0 |
| | Weight ratio of dye to alkalizing agent | 0.24 | 0.24 | 0.24 | 0.24 | 0.24 | 0.24 |
| Evaluation | (L*, a*, b*, h) of powder | L*: −50.22<br>a*: 6.81<br>b*: −23.46<br>h: −14.12 | L*: −27.07<br>a*: 15.15<br>b*: −1.04<br>h: −7.90 | L*: −45.82<br>a*: 27.27<br>b*: −0.13<br>h: −13.54 | L*: −24.50<br>a*: 25.81<br>b*: 20.28<br>h: −7.45 | L*: −21.52<br>a*: 25.81<br>b*: 56.44<br>h: −4.64 | L*: −3.21<br>a*: −3.18<br>b*: 36.26<br>h: 1.06 |
| | (L*, a*, b*, h) of hair after hair dyeing | L*: −56.30<br>a*: 14.81<br>b*: −45.85<br>h: −43.05 | L*: −58.28<br>a*: 13.70<br>b*: −42.07<br>h: −40.54 | L*: −55.01<br>a*: 42.70<br>b*: 0.90<br>h: −29.37 | L*: −54.98<br>a*: 42.51<br>b*: 0.96<br>h: −28.81 | L*: −17.54<br>a*: 36.69<br>b*: 67.87<br>h: −15.70 | L*: −12.68<br>a*: 24.18<br>b*: 68.28<br>h: −10.78 |

TABLE 1-continued

|  | Example 5 | Comparative Example 5 | Example 6 | Comparative Example 6 | Example 7 | Comparative Example 7 |
|---|---|---|---|---|---|---|
| dh | 28.9 | 32.6 | 15.8 | 21.4 | 11.1 | 11.8 |
| dE* | 18.3 | 42.1 | 6.73 | 27.0 | 13.4 | 37.0 |

As illustrated in the examples of table 1, the presence of alkanolamines reduced the color difference between powder composition and dyed hair for all three HC dyes. Powder compositions comprising sodium carbonate had a very strong color difference between powder and colored hair. Thus, this effect allows for better predicting the hair color when using the powder composition of the present invention.

TABLE 2

|  |  | Example 8 | Example 9 | Example 10 | Example 11 | Example 12 |
|---|---|---|---|---|---|---|
| Composition (% by weight) | HC Blue 18 | 2.0 | 0.2 | 10.0 | 2.0 | 2.0 |
|  | 2-amino methyl propanol | 8.4 | 8.4 | 25.0 | 2.0 | 8.4 |
|  | Ethanol | — | — | — | — | 9.0 |
|  | Diatomaceous earth | Ad 100.0 | Ad 100.0 | Ad 100 | Ad 100 | Ad 100 |
|  | Weight ratio of dye to alkalizing agent | 0.24 | 0.02 | 0.40 | 1.0 | 0.24 |
| Evaluation | (L*, a*, b*, h) of powder | L*: −50.22 a*: 6.81 b*: −23.46 h: −14.12 | L*: −33.76 a*: 1.80 b*: −32.34 h: −16.63 | L*: −59.12 a*: 1.83 b*: −6.32 h: 2.13 | L*: −42.60 a*: 7.51 b*: −20.20 h: −13.09 | L*: −53.50 a*: 6.93 b*: −21.46 h: −13.48 |
|  | (L*, a*, b*, h) of hair after hair dyeing | L*: −56.30 a*: 14.81 b*: −45.85 h: −43.05 | L*: −54.00 a*: 13.42 b*: −46.36 h: −43.18 | L*: −60.70 a*: 15.46 b*: −43.47 h: −41.69 | L*: −56.29 a*: 6.73 b*: −29.83 h: −30.44 | L*: −56.11 a*: 15.32 b*: −44.42 h: −42.26 |
|  | dh | 28.9 | 26.6 | 43.8 | 17.4 | 28.8 |
|  | dE* | 18.3 | 25.7 | 16.8 | 16.4 | 15.1 |

As illustrated in the examples 8 to 11, different weight ratios of alkanolamines and HC dyes allowed for minimizing the color difference between powder composition and dyed hair. Moreover, the presence of certain amount of solvent, namely ethanol, still yielded a freely-flowing powder and showed minimal color differences between powder and dyed hair.

The following examples are within the scope of the present invention. All compositions comprise less than 1% by weight water.

Example 13

| Ingredient | % by weight |
|---|---|
| Aminomethyl propanol | 7.5 |
| HC Red 18 | 2.0 |
| HC Yellow 16 | 0.5 |
| HC Blue 18 | 0.3 |
| Corn starch | 9.0 |
| Bentonite | 9.0 |
| Aerosil | 1.0 |
| Nylon powder | to 100 |

Example 14

| Ingredient | % by weight |
|---|---|
| Aminomethyl propanol | 8.0 |
| HC Red 18 | 1.0 |
| HC Red 3 | 0.1 |
| Basic yellow 87 | 0.2 |
| Polysilicone-9 | 0.1 |
| Ammonium bicarbonate | 1.0 |
| Polyquaternium-10 | 1.0 |
| Aerosil | 1.3 |
| Disodium EDTA | 1.0 |
| Nylon powder | to 100 |

Example 15

| Ingredient | % by weight |
|---|---|
| Aminomethyl propanol | 5.0 |
| HC Red 18 | 1.0 |
| HC Yellow 16 | 0.1 |
| HC Blue 18 | 1.0 |
| Amodimethicone | 0.1 |
| Guanidine bicarbonate | 1.0 |
| Sodium metasilicate | 1.0 |
| Paraffin oil | 7.5 |
| EDTA di sodium | 2.5 |
| Xanthan gum | 1.0 |
| Sodium lauryl sulphate | 1.5 |

-continued

| Ingredient | % by weight |
|---|---|
| Aerosil 280 | 2.0 |
| Sawdust | to 100 |

Example 16

| Ingredient | % by weight |
|---|---|
| Monoethanolamine | 5.0 |
| HC Blue 17 | 1.0 |
| Acid red 52 | 0.1 |
| DC Yellow 10 | 0.2 |
| Sodium lauryl sulphate | 0.2 |
| Amodimethicone | 0.1 |
| Xanthan gum | 0.8 |
| Diatomaceous Earth | to 100 |

Example 17

| Ingredient | % by weight |
|---|---|
| Aminomethyl propanol | 5.0 |
| HC Red 18 | 1.0 |
| HC Blue 18 | 0.8 |
| Basic red 51 | 0.5 |
| Sodium cocoamphoacetate | 0.2 |
| Diatomaceous Earth | to 100 |

Example 18

| Ingredient | % by weight |
|---|---|
| Aminomethyl propanol | 5.0 |
| Acid red 52 | 1.0 |
| Basic Red 51 | 0.5 |
| PEG-40 Hydrogenated castor oil | 0.2 |
| Polysilicone-9 | 0.1 |
| Fragrance | 0.5 |
| Diatomaceous Earth | to 100 |

Example 19

| Ingredient | % by weight |
|---|---|
| Monoethanolamine | 6.0 |
| Acid Red 52 | 1.0 |
| Acid yellow 2 | 0.2 |
| PEG-60 Hydrogenated castor oil | 0.2 |
| Paraffin oil | 4.5 |
| Diatomaceous Earth | to 100 |

Example 20

| Ingredient | % by weight |
|---|---|
| Monoethanolamine | 5.5 |
| Acid Red 52 | 0.5 |
| DC Yellow 10 | 1.5 |
| Behentrimonium chloride | 0.2 |
| Paraffin oil | 4.5 |
| Diatomaceous Earth | to 100 |

Example 21

| Ingredient | % by weight |
|---|---|
| Monoethanolamine | 5.0 |
| Acid Red 52 | 2.0 |
| DC Yellow 10 | 0.6 |
| HC Blue 17 | 0.4 |
| PEG-60 | 0.2 |
| Paraffin oil | 4.5 |
| Diatomaceous Earth | to 100 |

Example 22

| Ingredient | % by weight |
|---|---|
| Aminomethyl propanol | 5.0 |
| HC Red 18 | 0.4 |
| HC Yellow 16 | 0.1 |
| HC Blue 18 | 1.0 |
| Paraffin oil | 4.5 |
| Diatomaceous Earth | to 100 |

Example 23

| Ingredient | % by weight |
|---|---|
| Aminomethyl propanol | 5.0 |
| HC Red 18 | 0.01 |
| Nylon powder | 9.9 |
| Paraffin oil | 4.5 |
| Diatomaceous Earth | to 100 |

The same red color was achieved with 0.1%, 0.2%, 0.25%, and 0.5%, and 9% of aminomethyl propanol.

Example 24

| Ingredient | % by weight |
|---|---|
| Aminomethyl propanol | 5.0 |
| HC Red 18 | 0.4 |
| HC Yellow 16 | 0.1 |
| HC Blue 18 | 1.0 |
| Corn starch | 3.0 |
| Paraffin oil | 4.5 |
| Diatomaceous Earth | to 100 |

The invention claimed is:

1. A powder composition, comprising:
   at least one direct dye selected from the group consisting of HC Red 18, HC Blue 18 and HC Yellow 16;
   at least one alkanolamine as an alkalizing agent; and
   an organic and/or inorganic pulverulent excipient,
   wherein the composition is suitable for treating keratin fibers.

2. The composition according to claim 1, which comprises water in an amount of 10% or less by weight, calculated to the total weight of the composition.

3. The composition according to claim 1, further comprising:
   at least one solvent selected from the group consisting of water, ethanol, N-propanol, isopropanol, and a mixture thereof.

4. The composition according to claim 1, further comprising:
   a second alkalizing agent other than the at least one alkanolamine,
   wherein the second alkalizing agent is at least one of carbonate and/or bicarbonate salts with cations selected from the group consisting of sodium, potassium, ammonium and guanidine.

5. The composition according to claim 1, wherein a weight ratio of a total concentration of HC Red 18, HC Blue 18 and HC Yellow 16 to a total concentration of the at least one alkanolamine is in the range of 0.01 to 5.

6. The composition according to claim 1, wherein the composition is free of persalts.

7. The composition according to claim 1, wherein the at least one alkanolamine is at least one selected from the group consisting of monoethanolamine, diethanolamine, triethanolamine, monoethanol methylamine, monoethanol dimethylamine, di-ethanolmethylamine, monoethanolethylamine, monoethanoldiethylamine, diethanolethylamine, monoethanolpropylamine, monoethanoldipropylamine, diethanolpropylamine, monoethanolbutylamine, diethanolbutylamine and 2-amino-2-methylpropanol.

8. The composition according to claim 1, wherein the at least one alkanolamine is 2-amino-2-methylpropanol and/or monoethanolamine.

9. The composition according to claim 1, further comprising:
   sodium metasilicate as a third alkalizing agent.

10. The composition according to claim 1, wherein a total concentration of the at least one direct dye is in the range of 0.01% to 10% by weight, calculated to the total weight of the composition.

11. The composition according to claim 1, wherein a total concentration of alkalizing agents is in the range from 1% to 30% by weight, calculated to the total weight of the composition.

12. The composition according to claim 1, wherein the pulverulent excipient is at least one selected from the group consisting of diatomaceous earth, kaolin, bentonite, starch nylon powder, montmorillonit, gypsum, sawdust, and perlite.

13. The composition according to claim 1, wherein a total concentration of the pulverulent excipient is in the range of 50% to 98% by weight, calculated to the total weight of the composition.

14. The composition according to claim 1, further comprising:
   a liquid dust binding and/or granulating agent.

15. A method for coloring keratin fibers, comprising:
   mixing the composition according to claim 1 into an aqueous composition comprising at least one conditioning ingredient immediately prior to application onto hair;
   applying thus obtained composition onto hair and leaving it on the hair for a period from 1 to 45 min;
   rinsing-off the composition from the hair;
   optionally shampooing the hair; and
   optionally drying the hair.

16. The method according to claim 15, wherein the aqueous composition comprises hydrogen peroxide.

17. A method for bleaching and colouring keratin fibers, comprising:
   mixing the composition according to claim 1 with two other
   compositions wherein one of the compositions is an anhydrous powder composition comprising one or more persalts and the other composition is an aqueous composition comprising one or more oxidizing agent;
   applying thus obtained composition onto hair and leaving it on the hair for a period from 1 to 45 min;
   rinsing-off the composition from the hair;
   optionally shampooing the hair; and
   optionally drying the hair.

18. A kit for hair, comprising:
   a powder composition according to claim 1; and
   an aqueous composition.

19. The kit according to claim 18, wherein the aqueous composition is at least one individually packed composition selected from the group consisting of
   an aqueous composition comprising one or more conditioning ingredients,
   an aqueous composition comprising one or more alkalizing agents,
   an aqueous composition comprising one or more oxidative dye precursors,
   an aqueous composition comprising one or more oxidizing agents, and
   an anhydrous powder composition comprising one or more persalts.

* * * * *